United States Patent [19]

Hori

[11] Patent Number: 4,519,399
[45] Date of Patent: May 28, 1985

[54] METHOD FOR MEASURING THE DEGREE OF NASALITY

[75] Inventor: Kiyoharu Hori, Hino, Japan

[73] Assignee: Rion Kabushiki Kaisha, Japan

[21] Appl. No.: 557,536

[22] Filed: Dec. 2, 1983

[30] Foreign Application Priority Data

Dec. 13, 1982 [JP] Japan .................. 57-218210

[51] Int. Cl.³ .............................. A61B 5/00
[52] U.S. Cl. ................... 128/724; 128/725; 128/777; 128/630; 434/185
[58] Field of Search ............... 434/185; 128/773, 777, 128/720, 630, 725, 724

[56] References Cited

U.S. PATENT DOCUMENTS 3,281,534 10/1966 Dersch ..................... 128/630 X
3,867,770 2/1975 Davis ...................... 434/185
3,906,936 9/1975 Habal ...................... 128/724
3,946,504 3/1976 Nakano ..................... 434/185

FOREIGN PATENT DOCUMENTS 2841308 4/1980 Fed. Rep. of Germany ...... 434/185

Primary Examiner—Kyle L. Howell
Assistant Examiner—John C. Hanley
Attorney, Agent, or Firm—Leydig, Voit, Osann, Mayer and Holt, Ltd.

[57] ABSTRACT

A method of measuring the degree of nasality in human voice sounds by independently isolating and measuring without leakage the exhaled air flow rate through the nose and the exhaled air flow rate through the mouth of a person resulting from the utterance of a sound and determining the ratio of the two air flow rates.

8 Claims, 11 Drawing Figures

METHOD FOR MEASURING THE DEGREE OF NASALITY

TECHNICAL FIELD

The present invention relates to a method of measuring the degree of nasality in human voice sounds.

BACKGROUND ART

To measure the degree of nasality is important in the fields of otorhinolaryngology, dentistry and oral maxillo-facial surgery. For instance, a person with a cleft palate produces considerable nasal sounds compared with a person with a normal palate. If the degree of nasality is clearly indicated in terms of numerical figures, the degree of cleft palate can be objectively evaluated.

A nasality indicator has been proposed to numerically indicate the degree of nasality. This conventional nasality indicator will be described below with reference to FIG. 1. A vibration detector 1 is placed at a desired position on the face to detect vibrations that are produced in the nasal wall during the utterance of voice sounds that pass through the nasal cavity. At the same time a microphone 2 is disposed in front of the lips at a predetermined distance to detect the sound waves produced during the utterance. Outputs of the detector and microphone are then compared in accordance with the following relation (1) to find the degree of nasality.

$$\text{Degree of Nasality} = \frac{\text{Output Voltage of Vibration Detector}}{\text{Output Voltage of Microphone}} \quad (1)$$

As shown in FIG. 1, the individual outputs of the detector 1 and microphone 2 are amplified through amplifiers 3, 4, detected though detector/rectifier circuits 5, 6, applied to a comparison circuit 7, which determines the ratio V/S of the two outputs (V denotes an output level of the vibration detector 1 and S denotes an output level of the microphone 2), and the output of the V/S circuit 7 is indicated on a reading instrument 8.

FIG. 2 is a sectional view of the face which illustrates the paths for transmitting voiced sounds. The vibration detector 1 is installed on an upper side portion of the nose by suitable means, such as a double-sided adhesive tape or the like. The signals picked up by the vibration detector 1 consist of a signal b, which vibrates walls of a vocal tract when the phonated voice passes through the vocal tract and which is affected by resonance in the nasal cavity, and signals a, c, which are not affected by resonance in the nasal cavity. Here, the signal a, during phonation, is transmitted to the vibration detector 1 via an oral cavity, the signal b is transmitted to the vibration detector 1 via a nasal cavity, and the signal c is transmitted to the vibration detector 1 via paths other than via the oral and nasal cavities. The two arrows indicate voice paths.

The degree of nasality is given by:

$$V/S = (V_1 + V_2)/S$$

where $V_1$ denotes a signal level which is affected by resonance in the nasal cavity and $V_2$ denotes a signal level which is not affected by resonance in the nasal cavity. Therefore, if $V_2$ is significantly smaller than $V_1$, the degree of nasality is approximately given by $V_1/S$, i.e., the degree of nasality is nearly in proportion to the nasalized components. However, in the case of a person with a slight or intermediate cleft palate, the condition $V_1 \geq V_2$ often develops and the signal level $V_2$ is more significant. Therefore, the degree of nasality is not necessarily in proportion to the nasalized components. Thus, according to the conventional art, the degree of nasality is not exactly determined in all cases, i.e., the values are not clearly and exactly distinguishable for a person with a normal palate compared with a person with a slightly cleft palate.

According to the above-mentioned conventional method, furthermore, it is difficult to detect only pneumatic vibration which has passed through the nasal cavity by using the vibration detector. The vibration detector detects pneumatic vibration which passes through the vocal tract, rather than the nasal cavity, via the human tissue surrounding the vibration detector. Therefore, it is difficult to extract only nasalized sounds and the results are not exact.

DISCLOSURE OF THE INVENTION

The principal object of the present invention is to exactly determine the degree of nasality in numerical terms by measuring the exhaled air flow rate through the nasal cavity during phonation and comparing that rate with the exhaled air flow rate through the oral cavity.

As shown in FIG. 3, voiced sound is produced by increasing and decreasing the exhaled flow from the lungs past the vocal cords 11 and results in a source of voice. Among the voiced sounds, phonemes which are not nasalized, i.e., /t/, /k/, /p/, /s/, / /, and the like, are emitted from the lips 13 as sounds through the oral cavity 12. In the case of nasalized phonemes, such as /n/, /m/, and the like, the nasopharynx 14 is opened and the phonemes are emitted as sounds through the nasal cavity 15. In this case, part of the nasalized phonemes pass through the oral cavity 12 and are emitted as sounds.

Unvoiced sounds are produced by the hiss of the breath passing through constrictions, such as the lips, and articulating conditions of the tongue. For instance, plosives, such as /t/ and the like, are produced by completely closing the lips 13 and the uvula 14 to increase the exhaled air flow pressure from the lungs and by suddenly opening the lips. Thus, production of sound during phonation depends upon the flow process of the exhaled air. The present invention is based upon this fact and gives attention to the paths through which the exhaled air flows. More specifically, the method of the present invention compares the exhaled air flow rates to numerically determine the degree of nasality.

BRIEF DESCRIPTION OF THE DRAWINGS

In the drawings, the same reference numerals denote the same or corresponding portions.

BEST MODE FOR CARRYING OUT THE INVENTION

Figure 1:
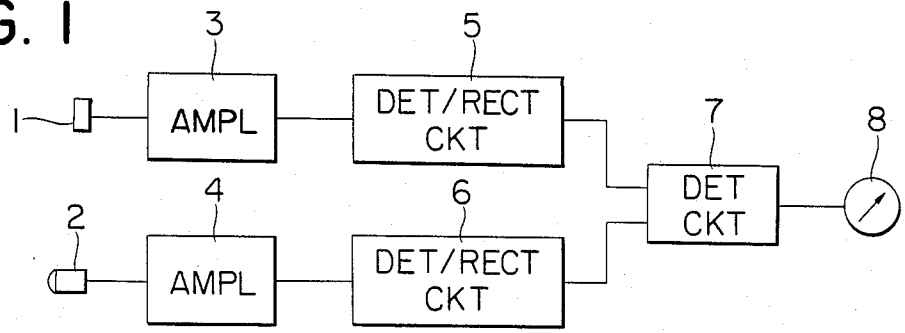
FIG. 1 is a block diagram of a conventional nasality indicator.
Figure 2:
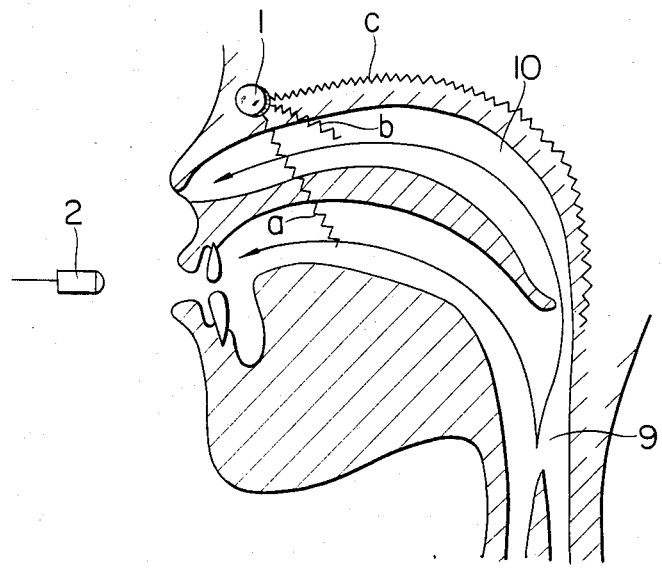
FIG. 2 is a sectional view of a face and illustrates the location of a microphone and vibration detector used in the conventional indicator system of FIG. 1.
Figure 3:
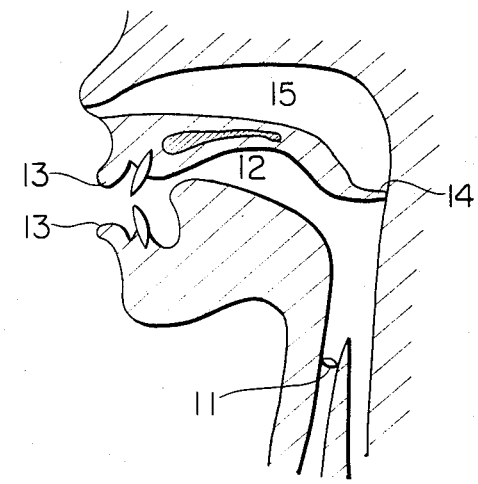
FIG. 3 is a sectional view of a face and illustrates the paths through which the voice air flows.
Figure 4:
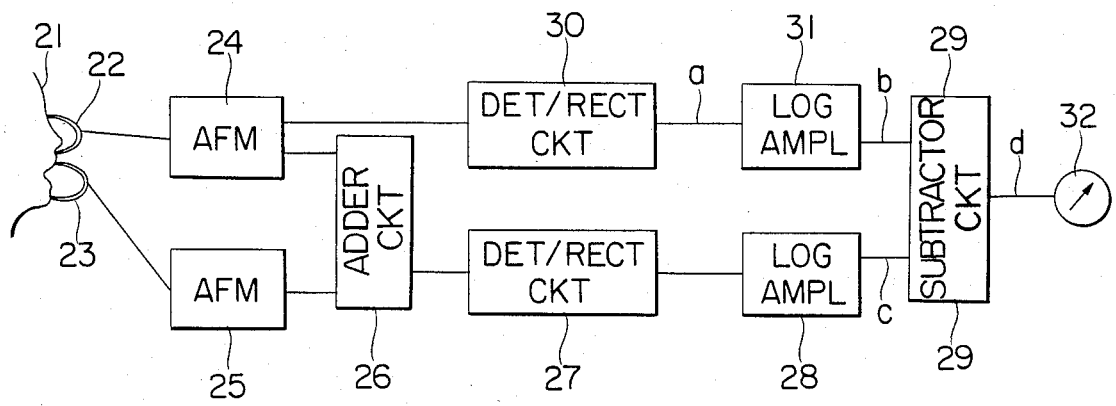
FIG. 4 is a block diagram which illustrates an embodiment of an electronic system for carrying out the method of the present invention.

Referring first to FIG. 4, to carry out the invention a human face 21 is provided with a nose cover 22 around the nasal cavity, i.e., the nose, and a lip cover 23 around the oral cavity, i.e., the lips, so that the exhaled air flows resulting from a phonation are independently isolated and received without leakage. The covers 22, 23 are made, for example, of flexible rubber in substantially a conical shape. In keeping with the invention, the covers 22, 23 are provided with air flow meters 24, 25 for measuring the exhaled air flow rates which result from a phonation and which are emitted into the covers 22, 23. Thus, the exhaled air flow rate which is emitted into the cover 22 through the nasal cavity is measured by the air flow meter 24 and the exhaled air flow rate which is emitted into the cover 23 through the oral cavity is measured by the air flow meter 25.

Electric voltage outputs from the air flow meters 24, 25, representing air flow rates, are applied to two input terminals of an adder circuit 26 where they are added together. This adder circuit 26 and the other circuits in the electronic systems described herein may be provided by operational amplifiers as disclosed, for example, in *Burr-Brown Operational Amplifiers*, McGraw-Hill Book Company, 1971. The adder circuit output is then applied to a detector/rectifier circuit 27 where it is detected and rectified and is converted into an output voltage which is a logarithmic function of the input voltage through a logarithmic amplifier 28 and is supplied to one of the two input terminals of a subtractor circuit 29. Another voltage output is taken from the flow meter 24, detected and rectified through a detector/rectifier circuit 30, converted into an output voltage which is a logarithmic function of the input voltage through a logarithmic amplifier 31, and is supplied to another input terminal of the subtractor circuit 29. Therefore, the subtractor circuit 29 produces a voltage output which is given according to the following relation (2):

Output of Subtractor Circuit 29 (on db scale)
= 20 log (exhaled air flow rate through nose)
− 20 log (exhaled air flow rate through mouth)
+ (exhaled air flow rate through nose)

$$= 20 \log \frac{\text{exhaled air flow rate through nose}}{\text{exhaled air flow rate through mouth} + \text{exhaled air flow rate through nose}}$$

The subtractor circuit 29 thus produces an output voltage constituting a logarithmic value which represents the ratio of an exhaled air flow rate through the nose to a total exhaled air flow rate occurring in the phonation. Accordingly, by supplying the output from the subtractor circuit 29 to a numerical indicator 32, the degree of nasality can be determined in numerical values. Similarly, if an instrument 32 having a visual indicator is connected to the subtractor circuit 29, the output can be determined and visually observed.

Figure 5:
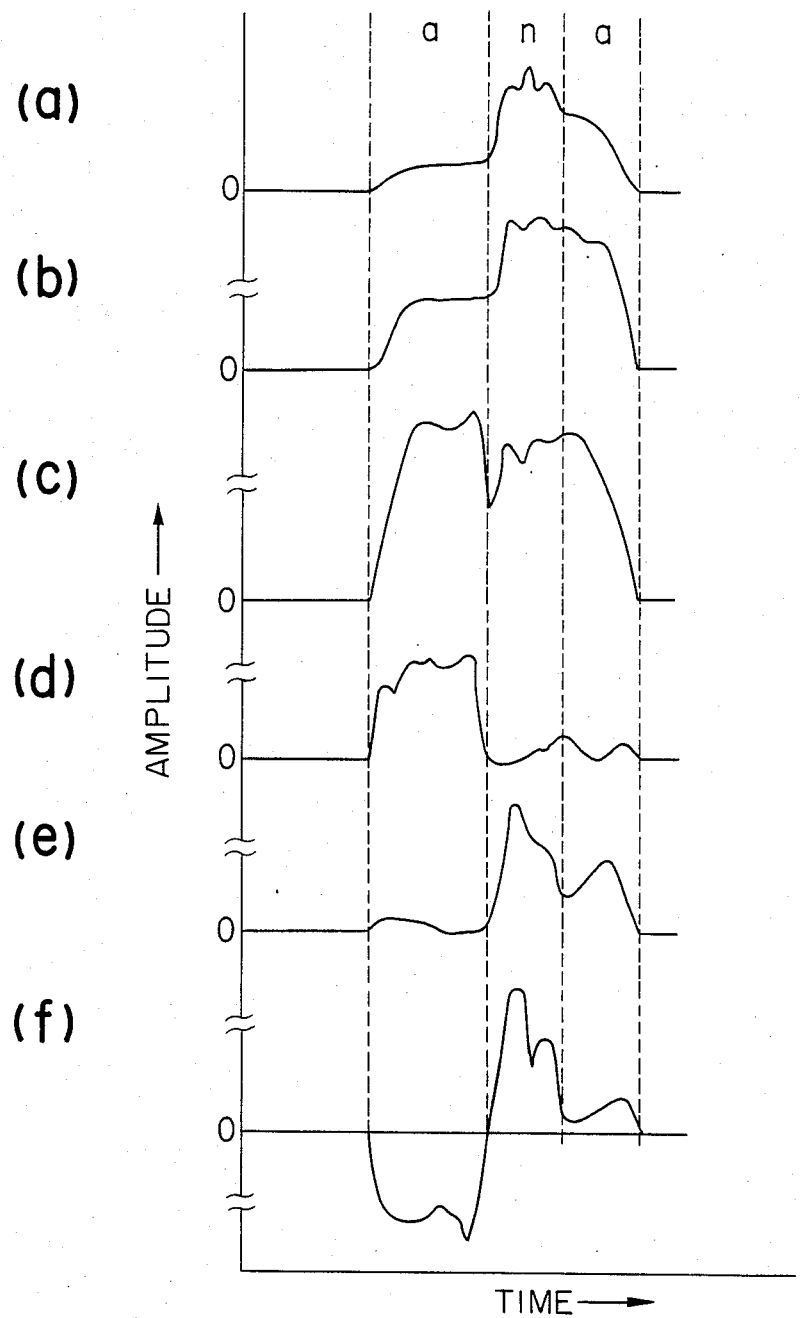
FIG. 5 is a time chart related to the embodiment of FIG. 4.

FIG. 5 is a time chart for the above-mentioned embodiment in which the diagram (a) shows an output waveform of the detector/rectifier circuit 30 when a sound [ana] is pronounced, the diagram (b) shows an output waveform of the logarithmic amplifier 28, and the diagram (d) shows an output waveform of the subtractor circuit 29. As will be clear from the output waveform (d), the nasalized voice [na] has a low amplitude and the first voice [a], which is not nasalized, has a high amplitude. Therefore, the two voices can be clearly distinguished from each other.

When it is simply required to distinguish nasalized voiced sounds from voiced sounds which are not nasalized, i.e., when it is not required to find the degree of nasality, the output from the air flow meters 24, 25 can be added and compared with the output from the air flow meter 25, representing air flow rate from the mouth only, which is an alternative to the above-mentioned embodiment, so that the subtractor circuit 29 produces an output which is given by the next relation:

$$20 \log \frac{\text{exhaled air flow rate through mouth}}{\text{exhaled air flow rate through mouth} + \text{exhaled air flow rate through nose}}$$

The subtractor circuit 29 produces an output waveform as shown in FIG. 5(e); that is, the nasalized voice exhibits a high amplitude and the voice which is not nasalized exhibits a low amplitude. Therefore, this method also makes it possible to make distinctions.

In the previous system embodiment, the degree of nasality was numerically determined according to the relations:

$$\frac{\text{exhaled air flow rate through nose}}{\text{exhaled air flow rate through mouth} + \text{exhaled air flow rate through nose}}$$

or $$\frac{\text{exhaled air flow through mouth}}{\text{exhaled air flow rate through mouth} + \text{exhaled air flow rate through nose}}$$

Figure 6:
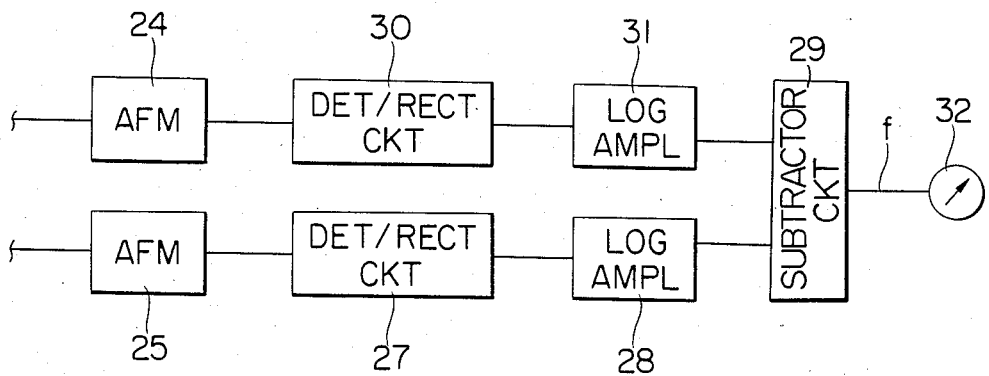
FIG. 6 is a block diagram which illustrates another embodiment of an electronic system for carrying out the method of the present invention.

According to a second system embodiment for carrying out the invention illustrated in FIG. 6, the degree of nasality is numerically determined according to the relations:

$$\frac{\text{exhaled air flow rate through nose}}{\text{exhaled air flow rate through mouth}}$$

or $$\frac{\text{exhaled air flow rate through mouth}}{\text{exhaled air flow rate through nose}}$$

To this end, the electric voltage output of the air flow meter 24 connected to the nose cover (not shown) is supplied to one of the two input terminals of the subtractor circuit 29 via the detector/rectifier circuit 30 and logarithmic amplifier 31. The electric voltage output of the air flow meter 25 connected to the lip cover (not shown) is supplied to the other input terminal of the subtractor circuit 29 via the detector/rectifier circuit 27 and the logarithmic amplifier 28. Therefore, the subtractor circuit 29 produces the output which is given by the following relation (3):

Output of Subtractor Circuit 29 (on db scale)
= 20 log (exhaled air flow rate through nose)
− 20 log (exhaled air flow rate through mouth)

$$= \frac{\text{exhaled air flow rate through nose}}{\text{exhaled air flow rate through mouth}}$$

Thus, the subtractor circuit 29 produces an output voltage which represents in logarithmic value the ratio of an exhaled air flow rate through the mouth and an exhaled air flow rate through the nose during a phonation. The degree of nasality is thus determined in numerical values. FIG. 5(f) shows an output waveform of the subtractor circuit 29. The nasalized voice appears on the plus side and the voice which is not nasalized appears on the minus side. It is, of course, possible to rearrange the component circuits so that the subtractor circuit 29 produces an output which is given by the next relation:

$$20 \log \frac{\text{exhaled air flow rate through mouth}}{\text{exhaled air flow rate through nose}}$$

In the embodiment shown in FIGS. 4 and 6, it may be desired to convert the analog outputs of air flow meters 24, 25 into digital quantities through A/D converters and process these outputs through a computer.

Figure 7:
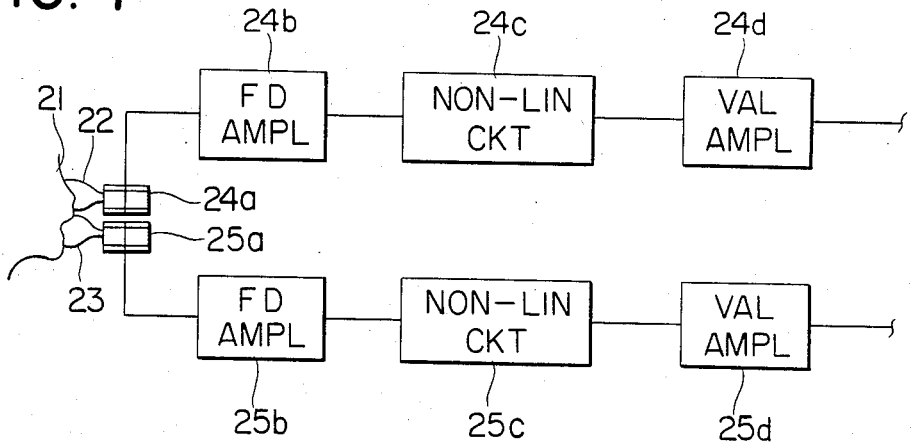
FIG. 7 is a block diagram of a system using hot-wire type air flow meters.
Figure 8:
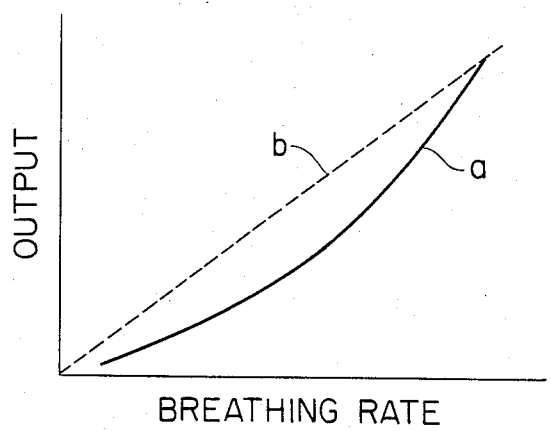
FIG. 8 is a diagram showing the relation between the exhaled air flow rate and the output in the embodiment of FIG. 7.

FIG. 7 is a diagram of a system including air flow meters of the hot-wire type that are particularly suited for carrying out the present invention. An air flow meter including a hot-wire 24a is employed for sensing an exhaled air flow rate through the nose and is connected to the nose cover 22. If an air flow rate sensor of the hot-wire type is used, the exhaled air flows out through the nasal cavity during the phonation and the resistance of the hot wire changes. This change is converted into a voltage change through a feedback amplifier 24b. In this case, due to the change of resistance because of air flow, the voltage drop across the hot-wire 24a corresponding to the exhaled air flow rate describes a curve of second degree as represented by a in FIG. 8. The curve a is interpolated into a straight line, as represented by b in FIG. 8, using a non-linear circuit 24c and is amplified through a variable amplifier 24d to adjust the degree of amplification such that a desired voltage is obtained. An air flow meter including a hot-wire 25a is employed for sensing an exhaled air flow rate through the mouth and is connected to the mouth cover 23. Like the air flow meter for the nose, the air flow meter for the mouth is connected to a feedback amplifier 25b, non-linear circuit 25c, and variable amplifier 25d. Amplification factors of the variable amplifiers 24d, 25d are adjusted so that the outputs can produce the same voltage change for the same air flow rate.

According to the present invention as described above, the exhaled air flow rate through the nose and exhaled air flow rate through the mouth are independently detected without leakage. It is, therefore, possible to extract the nasalized signals only and to numerically calculate the degree of nasality while maintaining high precision.

Figure 9A:
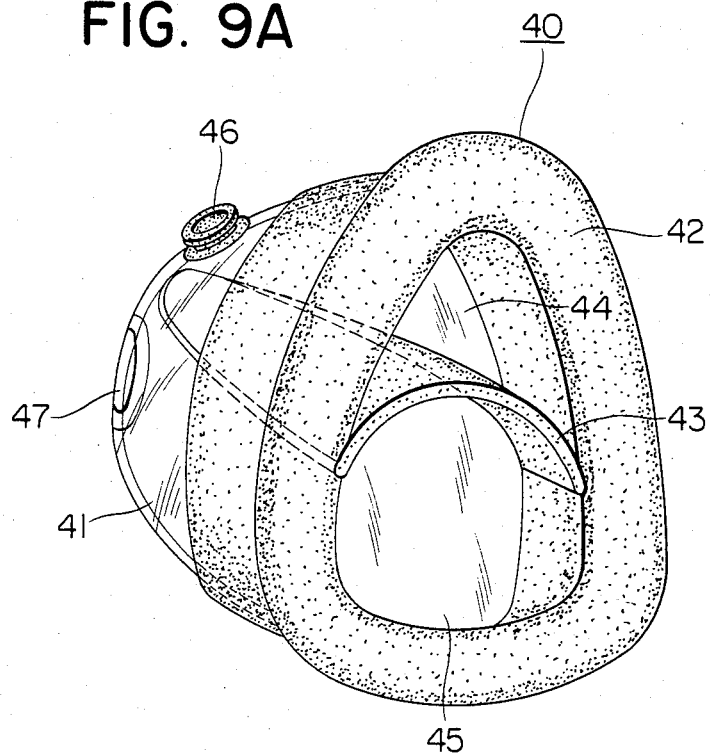
FIGS. 9A, 9B and 9C are a perspective view, a rear profile, and a cross-sectional profile, respectively, of a combined nose and mouth cover which may be used in carrying out the present invention.
Figure 9B:
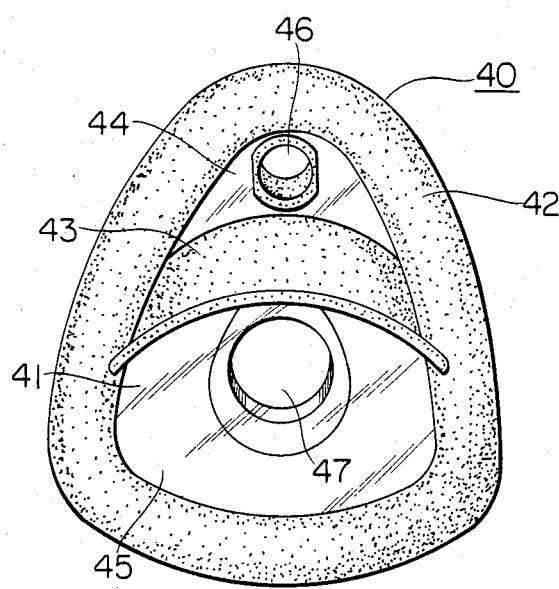
Figure 9C:
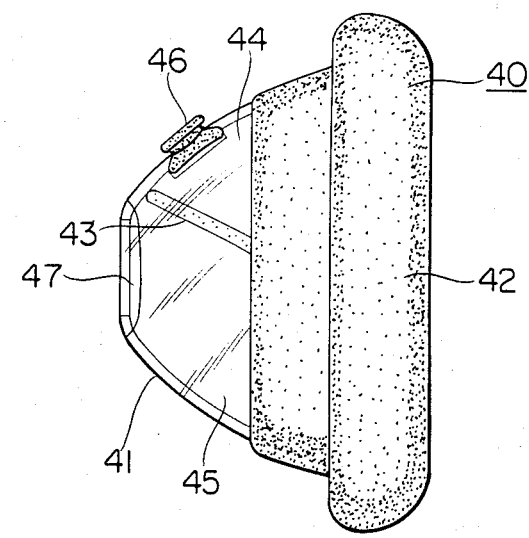

FIGS. 9A, 9B and 9C show various views of a combined nose and face cover 40 which may be used for the independent isolation without leakage of the flow rates of the air exhaled through the nose and mouth of a person wearing the cover. The cover 40 comprises a bowl-shaped container 41 made of a synthetic resin, a rubber seal portion 42 which is bonded to the bowl-shaped portion 41 and which contacts the face of the person wearing the cover 40, and a rubber separating plate 43 bonded to the bowl-shaped portion 41 and the rubber seal portion 42. The plate 43 divides the cover into exhaled air collection chambers 44, 45, separated from one another, for the independent collection of air exhaled from the nose and mouth, respectively. Exhaled air collection holes 46, 47 are formed in chambers 44 and 45, respectively, for transmitting air to a sensor, such as a hot-wire, for producing an output representing air flow rate. When the cover 40 is placed on the face of a person, the flow rate of air exhaled through his nose and mouth can be independently isolated and measured without leakage.

I claim:

1. Apparatus for measuring the degree of nasality in human voice sounds comprising means for independently isolating and measuring without leakage the exhaled air flow rate through the nose and the exhaled air flow rate through the mouth of a person resulting from a phonation, and means for determining the degree of nasality by comparing the air flow rates.

2. Apparatus for measuring the degree of nasality according to claim 1 including a unitary cover adapted to be sealed to the face of a person for receiving exhaled air flow without leakage from both the nose and mouth and having a divider for isolating the exhaled air flow of the nose from the mouth and transmitting the air flow to independent sensors for producing outputs representing air flow rates.

3. Apparatus for measuring the degree of nasality according to claim 1 including a cover for each of the nose and mouth adapted to be sealed to the face of a person for receiving exhaled air flow without leakage, each cover including a sensor for producing an independent output representing exhaled air flow rate.

4. A method of measuring the degree of nasality comprising the steps of independently isolating and measuring without leakage the exhaled air flow rate through the nose and the exhaled air flow rate through the mouth of a person resulting from a phonation and determining the degree of nasality by comparing the air flow rates.

5. A method of measuring the degree of nasality according to claim 4 wherein in comparing the air flow rates a value is obtained by dividing the exhaled air flow rate through the mouth by an output representing the exhaled air flow rate through the nose.

6. A method of measuring the degree of nasality according to claim 4 wherein in comparing the air flow rates a value is obtained by dividing an output representing the exhaled air flow rate through the nose by the exhaled air flow rate through the mouth.

7. A method of measuring the degree of nasality according to claim 4 wherein in comparing the air flow rates a value is obtained by dividing an output representing the exhaled air flow rate through the mouth by an output representing a value which is the sum of the exhaled air flow rate through the mouth and the exhaled air flow rate through the nose.

8. A method of measuring the degree of nasality according to claim 4 wherein in comparing the air flow rates a value is obtained by dividing an output representing the exhaled air flow rate through the nose by an output representing a value which is the sum of the exhaled air flow rate through the mouth and the exhaled air flow rate through the nose.

* * * * *